United States Patent
Tsuchiya et al.

(10) Patent No.: US 9,541,542 B2
(45) Date of Patent: Jan. 10, 2017

(54) METHOD OF DETECTING FILARIAL LARVAE IN BLOOD

(71) Applicant: Sysmex Corporation, Kobe-shi, Hyogo (JP)

(72) Inventors: Seiichiro Tsuchiya, Kobe (JP); Toshihiro Mizukami, Kobe (JP); Hideki Hirayama, Kobe (JP); Noriaki Nakajima, Kobe (JP); Ken Nishikawa, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 14/583,453

(22) Filed: Dec. 26, 2014

(65) Prior Publication Data

US 2015/0185201 A1    Jul. 2, 2015

(30) Foreign Application Priority Data

Dec. 26, 2013 (JP) ................. 2013-268996

(51) Int. Cl.
*G01N 33/49* (2006.01)
*C12Q 1/02* (2006.01)
*G01N 15/00* (2006.01)
*G01N 15/10* (2006.01)
*G01N 15/14* (2006.01)

(52) U.S. Cl.
CPC ............ *G01N 33/4915* (2013.01); *C12Q 1/02* (2013.01); *G01N 15/1436* (2013.01); *G01N 15/1459* (2013.01); *G01N 2015/008* (2013.01); *G01N 2015/0088* (2013.01); *G01N 2015/1006* (2013.01); *G01N 2015/1402* (2013.01); *G01N 2015/1477* (2013.01); *G01N 2333/4353* (2013.01)

(58) Field of Classification Search
None
See application file for complete search history.

(56) References Cited

U.S. PATENT DOCUMENTS

| 4,025,306 A | 5/1977 | Studer |
| 6,103,484 A | 8/2000 | Carlow et al. |
| 2005/0069959 A1* | 3/2005 | Yoshida ............ G01N 33/5094 435/7.2 |
| 2010/0248349 A1* | 9/2010 | Nakamura ........... G01N 15/147 435/287.2 |
| 2013/0273111 A1* | 10/2013 | Nutman ............. C07K 14/4354 424/265.1 |

FOREIGN PATENT DOCUMENTS

| EP | 2 233 909 A2 | 9/2010 |
| WO | WO 2012/061281 A1 | 5/2012 |

OTHER PUBLICATIONS

Yong W. Indirect Fluorescent Antibody Technique with Microfragments of W. bancrofti. Transactions of the Royal Society of Tropical Medicine and Hygiene 67(3)338-344, 1973.*
Aonuma H. et al. A Single Fluorescence Based LAMP Raction for Identifying Multiple Parasites in Mosquitoes. Experimental Parasitology 125(2)179-183, Jun. 2010.*
Pulak, R. "Techniques for Analysis, Sorting and Dispensing of *C. elegans* on the COPAS™ Flow-Sorting System", *Methods in Molecular Biology*, vol. 351, Feb. 1, 2006, pp. 275-286.
Sahu, B. et al., "A Flow Cytometry Based Method for Studying Embryogenesis and Immune Reactivity to Embryogenic Stages in Filarial Parasites", *Filaria Journal*, vol. 4, No. 1, Nov. 7, 2005, pp. 1-13.

* cited by examiner

*Primary Examiner* — Ralph Gitomer
(74) *Attorney, Agent, or Firm* — Brinks Gilson & Lione

(57) ABSTRACT

Disclosed is a method of detecting filarial larvae in blood. The method comprises preparing a measurement sample from a blood sample collected from an animal; flowing the prepared measurement sample through a flow cell; irradiating light on the measurement sample flowing through the flow cell; detecting light given off from the irradiated measurement sample; and detecting filarial larvae contained in the measurement sample based on characteristic parameter of the detected light.

14 Claims, 11 Drawing Sheets

US 9,541,542 B2

METHOD OF DETECTING FILARIAL LARVAE IN BLOOD

RELATED APPLICATIONS

This application claims priority under 35 U.S.C. §119 to Japanese Patent Application No. 2013-268996 filed on Dec. 26, 2013, the entire content of which is incorporated herein by reference.

BACKGROUND OF THE INVENTION

1. Field of the Invention

The present invention relates to a method of detecting filarial larvae in the blood of animals such as dogs, a blood analyzer, and a non-transitory computer-readable storage medium.

2. Description of the Related Art

Filariasis is a disease which is caused by the filarial parasites. Filariasis is particularly common in dogs, and is an infectious disease primarily caused via infection by mosquitoes. Filarial larvae reside in the bodies of infected animals. Microfilaria are one type of larvae present in the blood of infected animals. The microfilaria are transferred into the body of the mosquito when the mosquito ingests blood and while within the mosquito body become infectious larvae which are capable of transmitting the infection. When the mosquito ingests the blood of another animal, the infectious larvae is transferred to and infects the new host. The infectious larvae circulate through the blood stream to the heart of the host, where the parasite develops in the heart and pulmonary artery as it matures to adulthood.

Examinations for filariasis include a direct microscopic method wherein a blood sample is visually examined under a microscope (refer to U.S. Pat. No. 4,025,306), and a method using an immunological test kit to detect a specific antigen in the filarial infection sample (refer to U.S. Pat. No. 6,103,484).

Examination for filariasis by direct microscopy as mention above, however, requires visual observation of microfilaria in a blood sample by a veterinarian, which is labor intensive and time consuming and quite burdensome on the investigator. The antibody in the reagent utilized in examinations using the immunological test kit increases the cost and generally makes the reagent quite expensive.

Accordingly, it is desired to rapidly and inexpensively detect filarial larvae in blood while reducing the burden on the operator.

SUMMARY OF THE INVENTION

The scope of the invention is defined by the appended claims, and not by any statements within this summary.

An embodiment relates to a method of detecting filarial larvae in blood. The embodiment comprises: preparing a measurement sample from a blood sample collected from an animal; flowing the prepared measurement sample through a flow cell; irradiating light on the measurement sample flowing through the flow cell; detecting light given off from the irradiated measurement sample; and detecting filarial larvae contained in the measurement sample based on characteristic parameter of the detected light.

Another embodiment relates to a blood cell analyzer. The embodiment comprises: a sample preparing section configured to prepare a measurement sample from a blood sample collected from an animal; a flow cell that accepts the measurement sample prepared by the measurement sample preparing section; a light source for irradiating light on the measurement sample flowing through the flow cell; a light detector for receiving light given off from the measurement sample irradiated by the light source, and outputting a signal corresponding to amount of the received light; and a controller configured to detect filarial larvae in the measurement sample based on characteristic parameter included in the signal outputted from the light detector.

A further embodiment relates to a non-transitory computer-readable storage medium storing a program. The program causes a processor to execute operations comprising: obtaining measurement data which comprises characteristics parameter of light which is detected from a measurement sample flowing through a flow cell, the measurement sample being prepared from a blood sample collected from an animal; and detecting filarial larva in the measurement sample based on the characteristic parameter included in the obtained measurement data.

DETAILED DESCRIPTION OF THE PREFERRED EMBODIMENTS

The preferred embodiments of the present invention are described hereinafter with reference to the drawings. The method of the present embodiment detects filarial larvae of one type of microfilaria contained in blood collected from animals using an automated blood analyzer with an on-board flow cytometer.

[Structure of Blood Analyzer]

Figure 1:
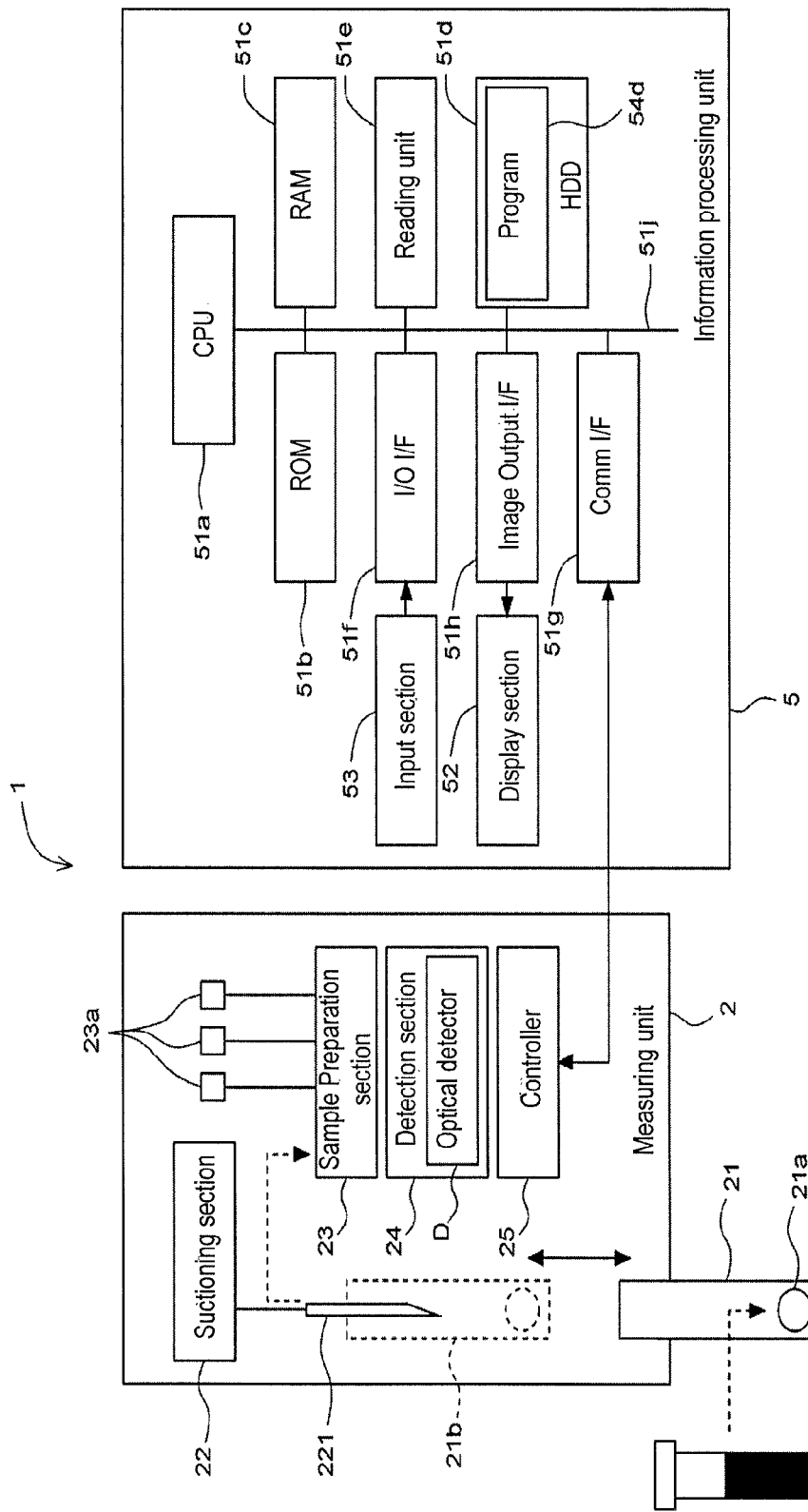
FIG. 1 shows the structure of the blood analyzer of the embodiment.

FIG. 1 is a schematic view showing the structure of an embodiment of the blood analyzer. The blood analyzer 1 of the present embodiment is a multi-item blood analyzer for use with animals which detects and counts each type of blood cell contained in a whole blood sample collected from an animal. The blood analyzer 1 is a multi-species type blood analyzer which operates in measurement modes corresponding to a specified animal species by receiving instructions of one animal species among various animal species such as dog, cat, rabbit and the like. As shown in FIG. 1, the blood analyzer 1 has a measuring unit 2, and an information processing unit 5 which is capable of controlling the measuring unit 2.

A whole blood sample of peripheral blood collected from an animal (for example, a dog) is contained in a sample container (collection tube) T. The whole blood sample contained in the sample container T is measured by the measuring unit 2. Note that the blood analyzer of the present embodiment is mainly used for examination of breeding and livestock animals such as dogs, cats and rabbits. When the term "animal" used in the specification should be understood to include humans.

<Structure of Measuring Unit>

The structure of the measurement unit is described below. As shown in FIG. 1, the measuring unit 2 has a sample container installation section 21 for receiving the sample container T within the housing of the measuring unit 2, a sample suctioning section 22 for suctioning the blood sample from the sample container T, a sample preparing section 23 for preparing a measurement sample to be used in measurements from the blood sample suctioned by the sample suctioning section 22, a detecting section 24 for detecting the blood cells in the measurement sample prepared by the sample preparing section 23, and a controller 25 configured by a CPU, memory and the like.

The sample container installation section 21 has a hole 21a for inserting the sample container T, and installation is accomplished by inserting the sample container T into the hole 21a. The sample container installation section 21 also is movable inside and outside of the housing of the measuring unit 2. The sample container T is taken into the measuring unit 2 by moving the sample container installation section 21 in which the sample container T is installed from the outside to the inside of the measuring unit 2. When the sample container T is discharged from the measuring unit 2, the sample container installation section 21 which accommodates the installed sample container T is moved from the inside to the outside of the measuring unit 2.

The sample container installation section 21 is movable to the suctioning position 21b within the measuring unit 2. When the sample container installation section 21 has been moved to the suctioning position 21b, the blood sample is suctioned from the sample container T by the sample suctioning section 22.

The sample suctioning section 22 has a suction tube 221. The sample suctioning section 22 also has a syringe pump (not shown in the drawing). The suction tube 221 is movable in vertical directions, and is configured to suction the blood sample within the sample container T at the suction position 21b by moving downward.

The sample preparing section 23 is provided with a mixing chamber which is not shown in the drawing. The suction tube 221 suctions a predetermined amount of the whole blood from the sample container T via the syringe pump, and the suctioned sample of the predetermined amount of whole blood is supplied to the mixing chamber by the syringe pump when the suction tube 221 is moved to the mixing chamber position. The sample preparing section 23 also is provided with a heater to heat the mixing chamber.

A reagent container 23a is connected via a tube to the sample preparing section 23. Specifically, a reagent container holding hemolytic agent, a reagent container holding staining reagent, and a reagent container holding sheath fluid diluting liquid) are connected to the sample preparing section 23. The hemolytic agent and staining reagent are used in the white blood cell classification and the microfilaria measurement which are described later. The hemolytic agent and the staining reagent are reagents for detecting microfilaria without using any immunological techniques. The phrase "without using immunological techniques" means that antibodies capable of recognizing and binding to cell surface antigens of the microfilaria are not used. These reagents from the reagent containers 23a are supplied to the mixing chamber of the sample preparing section 23.

The detecting section 24 has an optical detector D capable of performing white blood cell classifications and microfilaria measurements. The five subclasses of white blood cells present in the blood sample, that is, LYMPH (lymphocytes), EO (eosinophils), NEUT (neutrophils), BASO (basophils), and MONO (monocytes), are classified in the white blood cell classification and the microfilaria measurement. Also in the white blood cell classification and the microfilaria measurement, microfilaria in the blood sample are detected together with the five classes of white blood cells.

In the white blood cell classification and microfilaria measurements, the sample preparing section 23 prepares a measurement sample by mixing the whole blood sample, hemolytic agent and staining reagent, the prepared measurement sample is supplied to the optical detector D, and the characteristic parameters (fluorescent light intensity, forward scattered light intensity, forward scattered light pulse width) are detected by the optical detector D. The characteristic parameters obtained by measurement are supplied as measurement data to the information processing unit 3 through the controller 25, and white blood cells in the whole blood sample are detected and classified and the microfilaria are detected by the information processing unit 3 analyzing the measurement data.

Figure 2:
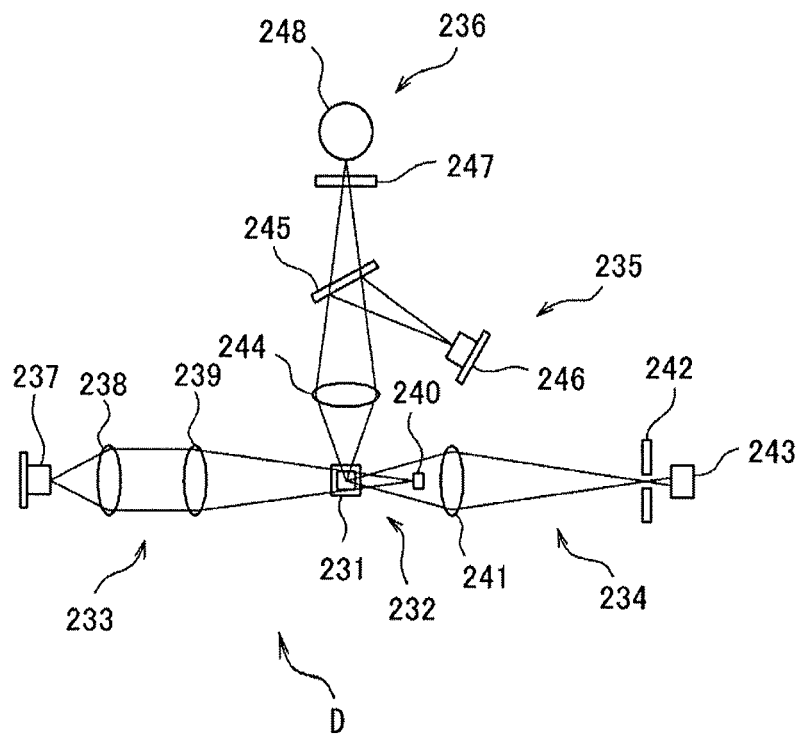
FIG. 2 shows essential structure of the optical detector.

FIG. 2 shows the essential structure of the optical detector D. The optical detector D supplies the measurement sample and sheath liquid to the flow cell 231 to create a liquid flowing through the flow cell 231 and the particles contained in the liquid flowing through the inside of the flow cell 231 are irradiated by laser light and measured; the optical detector D has a sheath flow system 232, beam spot forming system 233, forward scattered light receiving system 234, side scattered light receiving system 235, and fluorescent light receiving system 236.

The sheath flow system 232 is configured to create a flow of the measurement sample and the sheath liquid within the flow cell 231 so that the particles in the measurement sample are encapsulated in the sheath liquid. The beam spot forming system 233 is configured to irradiate the light emitted from a laser light source 237 on the flow cell 231 through a collimator lens 238 and condenser lens 239. The beam spot forming system 233 also has a beam stopper 240.

Figure 3:
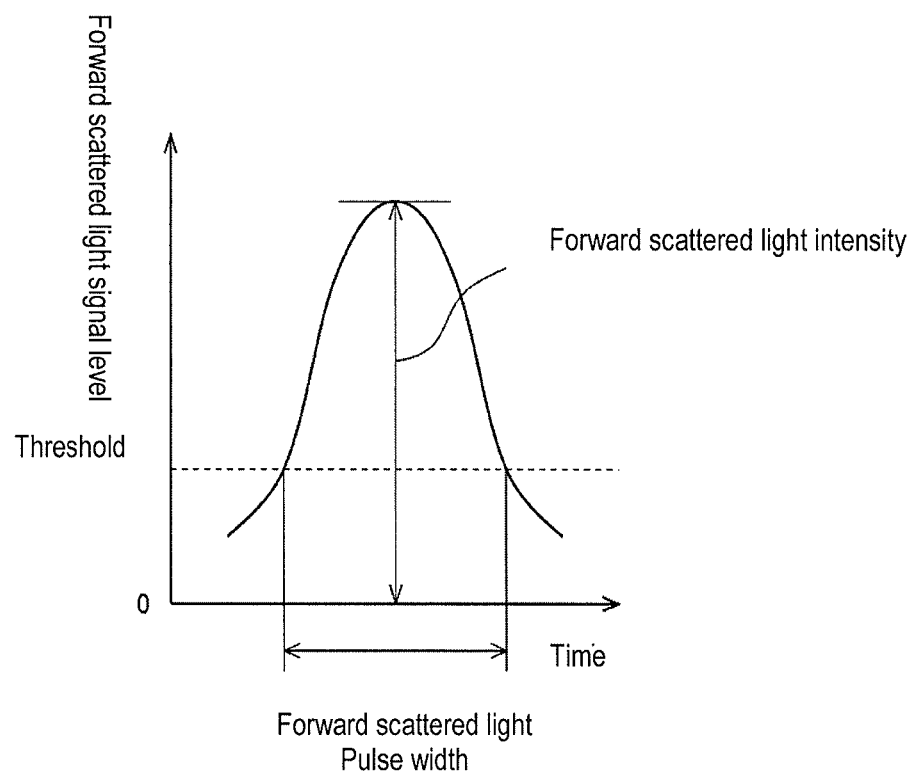
FIG. 3 is a graph of the pulse signals which schematically illustrate the characteristic parameters of the forward scattered light.

The forward scattered light receiving system 234 is configured to collect the scattered light traveling in the forward direction by a forward condensing lens 241, and the light passing through a pinhole 242 is received by the forward scattered light receiving section 243. The forward scattered light receiving section 243 outputs pulse signals corresponding to the intensity of the received forward scattered light. FIG. 3 is a graph which schematically shows the pulse signals output by the forward scattered light receiving section 243. As shown in the drawing, the peak height of the pulse which exceeds a predetermined threshold value is the forward scattered light signal intensity, and the pulse width which exceeds the predetermined threshold value is the forward scattered light pulse width. A photodiode or photomultiplier tube may be used as the forward scattered light receiving section 243.

A side scattered light receiving system 235 is configured to collect the scattered light traveling in the side direction by a side condensing lens 244, and part of the light is reflected by a dichromatic mirror 245 and received by a side scattered light receiving section 246. The side scattered light receiving section 246 outputs pulse signals corresponding to the intensity of the received side scattered light. Similar to the description of FIG. 3, the peak height of the pulse which exceeds a predetermined threshold value is the side scattered light signal intensity, and the pulse width which exceeds the predetermined threshold value is the side scattered light pulse width. A photodiode or photomultiplier tube may be used as the side scattered light receiving section 246.

Light scattering is a phenomenon that occurs when particles are present as obstructions in the direction in which the light is traveling, and alters the direction of travel of the light. Information relating to the size and composition of the particle can be obtained by detecting the scattered light. The forward scattered light intensity reflects the size and surface area of the particle. The side scattered light intensity reflects the complexity of the particle interior (shape of the nucleus, size of the nucleus, density, and degree of granularity). The forward scattered light pulse width reflects time required for the particle to pass the beam spot, that is, the total length of the particle.

Microfilaria have a filamentous elongated shape such that the total length is longer than the white blood cells and other blood cells. Therefore, the pulse width of the forward scattered light when microfilaria pass through the sheath flow cell 231 is greater than the pulse width of the forward scattered light when blood cells, including white blood cells, pass through the sheath flow cell 231. The forward scattered light pulse width therefore is particularly well suited to detect microfilaria. Since the side scattered light pulse width also reflects particle properties substantially similar to the forward scattered light pulse width, the side scattered light pulse width also may be used instead of the forward scattered light pulse width to detect microfilaria.

The fluorescent light receiving system 236 is configured so that a fluorescent light receiving section 248 receives the light which has passed through the dichroic mirror 245 and a spectral filter 247. The fluorescent light receiving section 248 outputs pulse signals corresponding to the intensity of the received fluorescent light. Similar to the description of FIG. 3, the peak height of the pulse which exceeds a predetermined threshold value is the fluorescent light intensity, and the pulse width which exceeds the predetermined threshold value is the fluorescent light pulse width. A photodiode, avalanche photodiode, or photomultiplier tube may be used as the fluorescent light receiving section 248.

When the whole blood sample is mixed with hemolytic agent and staining reagent, the nucleus of the blood cell is stained and fluorescent material is adhered to the microfilaria via the fluorescent material contained in the staining reagent. Generally, the nucleus of the blood cell is more strongly stained than microfilaria. When the particles (blood cells or microfilaria) stained by fluorescent material are irradiated with light, light of a longer wavelength than the wavelength of the irradiating light is given off by the particle. The intensity of the fluorescent light is intensified by staining, and information relating to the degree of staining of the particle can be obtained by measuring the fluorescent light intensity. The difference in the fluorescent light intensities can be used to detect microfilaria and classify white blood cells.

The detecting section 24 converts the analog pulse signals output by the light receiving sections 243, 246, and 248 of the optical detector D to digital signals, which are then transmitted to the controller 25.

The controller 25 is configured by a CPU, memory and the like, and controls each part of the measuring unit 2 by executing a control program. The controller 25 has a communication section which is not shown in the drawings, and is capable of data communication with the information processing unit 3. The pulse signal which has undergone A/D conversion by the detecting section 24 is transmitted to the controller 25 which analyzes the waveform and determines the characteristic parameters of each particle and creates measurement data that is then transmitted to the information processing unit 3 as described in FIG. 3. The characteristic parameters of each particle include the fluorescent light intensity, fluorescent light pulse width, forward scattered light intensity, forward scattered light pulse width, side scattered light intensity, and side scattered light pulse width.

<Structure of Information Processing Unit>

The structure of the information processing unit 5 is described below. The information processing unit 5 is configured by a computer. As shown in FIG. 1, the computer 5 is provided with a CPU 51a, ROM 51b, RAM 51c, hard disk 51d, reading device 51e, I/O interface 51f, communication interface 51g, and image output interface 51h; the CPU 51a, ROM 51b, RAM 51c, hard disk 51d, reading device 51e, I/O interface 51f, communication interface 51g, and image output interface 51h are connected by a bus 51j.

The hard disk 51d holds various installed computer programs that are executed by the CPU 51a, including an operating system and application programs, as well as the data used when executing these computer programs. The computer program 54a for measurement data analysis (to be described later) is also installed on the hard disk 51d. Application programs stored on the hard disk 51d have a plurality of measurement modes which correspond to a plurality of animal species such as dog, cat, and rabbit. More specifically, measurement modes for various animal species are set when the application program is actuated and the operator selects one animal species from among a plurality of animal species. Program codes based on the measurement sequence and analysis algorithms of each measurement mode are stored on the hard disk 51d, and the CPU 51a reads the program code corresponding to the set measurement mode and performs control of the measuring unit 2 and analysis of the measurement data obtained from the measuring unit 2 based on the read program code. The computer program 54a of the present embodiment operates on the operating system stored on the hard disk 51d.

The reading device 51e is configured by a flexible disk drive, CD-ROM drive, DVD-ROM drive or the like. The reading device 51e read the computer program 54a from a portable recording medium such as a CD or DVD on which the computer program 54a is stored, and install the computer program 54a on the hard disk 51d so that the computer functions as the information processing unit 5.

The input section 53 is configured by a keyboard, mouse, touchscreen or the like and is connected to the I/O interface 51f, and data may be input to the computer 5a by the operator using the input section 53. Inputting the animal species mentioned above is accomplished by the operator using the input section 53 and is transmitted to the CPU 51a.

The communication interface 51*fg* is connected to the controller 25 of the measuring unit 2 via a LAN. Hence, the information processing unit 5 can transmit operating instruction data and receive measurement data to/from the measuring unit 2.

The image output interface 51*h* is connected to the display section 52 configured by an LCD or CRT or the like, so that image signals corresponding to image data received from the CPU 51*a* are output to the display section 52. The display section 52 displays images based on the input image signals.

<Blood Analyzer Measurement Operation>

The operation of the blood analyzer 1 of the present embodiment is described below.

Figure 4:
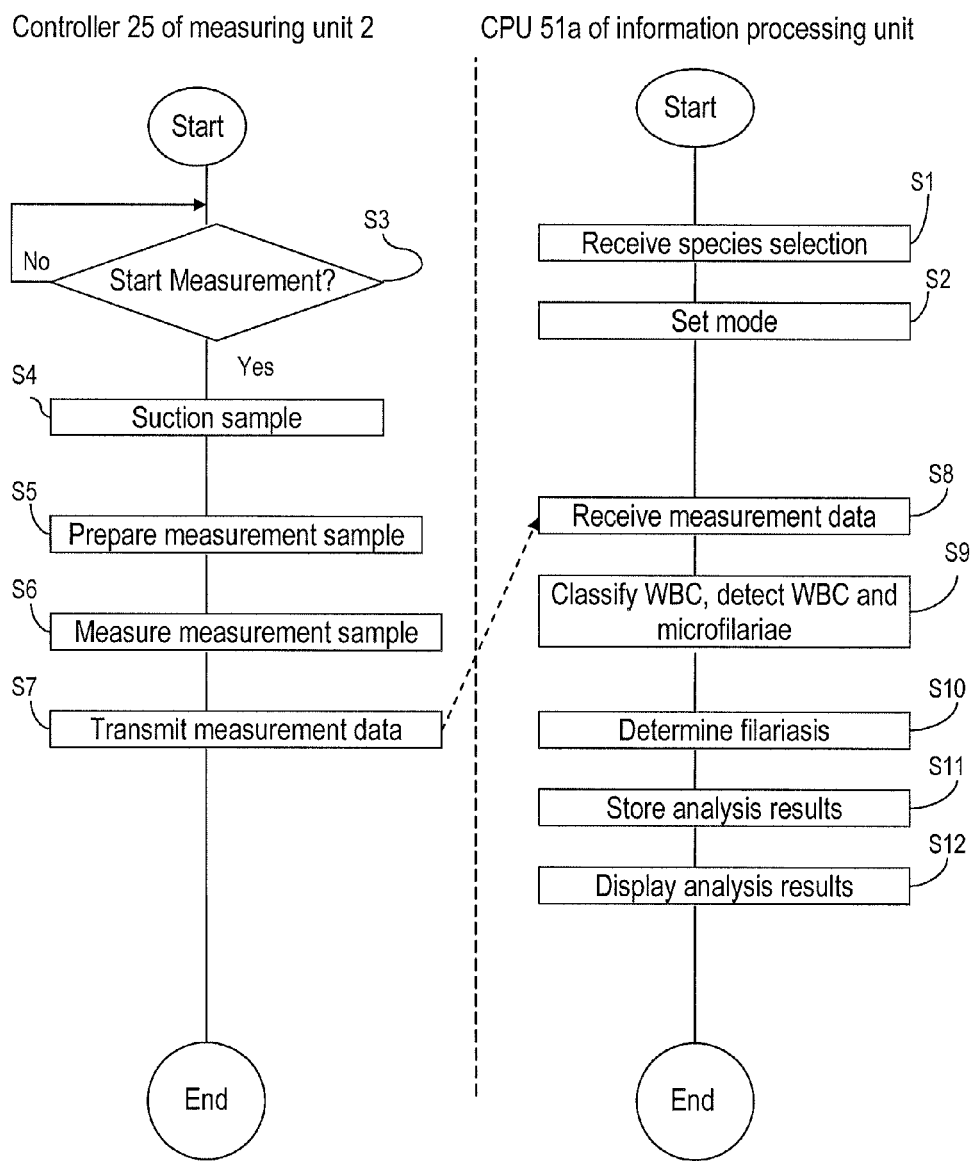
FIG. 4 is a flow chart of the operating sequences of the white blood cell classification and microfilaria detection measurement of the blood analyzer.

FIG. 4 is a flow chart of the operating sequences of the white blood cell classification and microfilaria detection measurement of the blood analyzer 1. The CPU 51*a* of the information processing unit 5 first displays a species selection screen on the display section 52, and receives the species selection input by the operator (Step S1). When the species is input, the CPU 51*a* sets the measurement mode corresponding to the input species (Step S2). Then, the controller 25 of the measuring unit 2 awaits the instruction to start the measurement (Step S3). The measurement start instruction is transmitted by pressing a measurement start switch (not shown in the drawing) provided on the measuring unit 2. The controller 25 repeats the process of step S3 when the measurement start switch is not pressed (Step S3: NO).

The operator inserts the sample container T containing a whole blood sample collected from an animal such as a dog into the hole 21*a* of the sample container installation section 21 on the outside of the measuring unit 2, and presses the measurement start switch (Step S3: YES). The sample measurement operation is thus started.

When the sample measurement operation starts, the sample container installation section 21 is retracted into the measuring unit 2, and the sample container T therefore is brought into the measuring unit 2. When the sample container installation section 21 is moved to the suctioning position 21*b*, the suction tube 221 is inserted into the interior of the sample container T and the whole blood sample is suctioned (Step S4).

Then, in the measuring unit 2, the measurement sample is prepared by controls initiated by the controller 25 (Step S5). In this process, a predetermined amount of whole blood sample previously suctioned by the sample suctioning section 22 is supplied to the mixing chamber of the sample preparing section 23, hemolytic agent and staining reagent are also supplied from the reagent containers 23*a* to the mixing chamber 23, and the whole blood sample, hemolytic agent, and staining reagent are mixed in the mixing chamber 23 to produce the measurement sample.

The prepared measurement sample is then subjected to optical measurements performed by the optical detector D. Specifically, in the process of step S6, the measurement sample and sheath liquid are simultaneously supplied to the flow cell 231 of the optical detector D while the flow cell 231 is irradiated by laser light from the laser light source 237, and at this time the generated forward scattered light is received by the forward scattered light receiving section 243, the side scattered light is received by the side scattered light receiving section 246, and the fluorescent light is received by the fluorescent light receiving section 248. The output signals (analog signals) from each light receiving element of the optical detector D are converted to digital signals by an A/D converter of the detecting section 24, and predetermined signal processing is performed by a signal processing circuit of the detecting section 24, then the processed signals are transmitted to the controller 25 as digital signals. The controller 25 extracts each characteristic parameter including forward scattered light intensity, forward scattered light pulse width, side scattered light intensity, fluorescent light intensity from the digital signals, and generates measurement data which include these characteristic parameters. The controller 25 then transmits the measurement data to the information processing unit 5 (step S7).

The information processing unit 5 of the blood analyzer 1 receives the measurement data from the measuring unit 2 (step S8).

In step S9, the CPU 51*a* classifies the white blood cells into five subclasses using the measurement data, and counts the number of blood cells in each subclass. In the process of step S9, the microfilaria are discriminated from blood cells and the number of detected microfilaria is counted.

Figure 5:
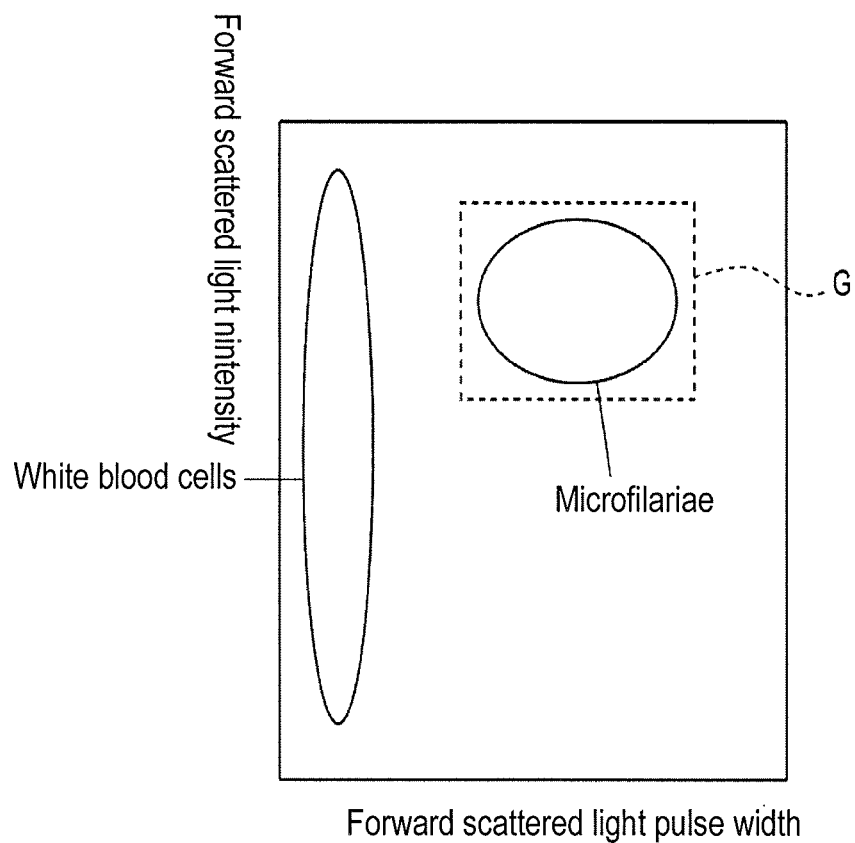
FIG. 5 is a scattergram of the forward scattered light pulse width and forward scattered light intensity in the measurement data.

The process of step S9 is described in detail. FIG. 5 schematically shows the regions of appearance of clusters in a scattergram plotted with the forward scattered light intensity and forward scattered light pulse width as the axes. In the scattergram of FIG. 5, the cluster of microfilaria and the cluster of white blood cells appear at mutually exclusive positions. As mentioned above, microfilaria appear in the region of high values for the forward scattered light pulse width compared to white blood cells because the total length of the microfilaria is longer than that of the white blood cells. The position at which microfilaria appear in the scattergram is determined by the forward scattered light pulse width and the forward scattered light intensity. In the present embodiment, therefore, a gate G (detection region) used to detect microfilaria is preset. The numerical range defining the microfilaria detection gate G is stored on the hard disk 51*d*. In the process of step S9, the CPU 51*a* detects as microfilaria those particles for which the values of the forward scattered light pulse width and the forward scattered light intensity are within the numerical range defined as the microfilaria detection gate G. Also in the process of step S9, the CPU 51*a* counts the number of microfilaria thus detected.

Figure 6:
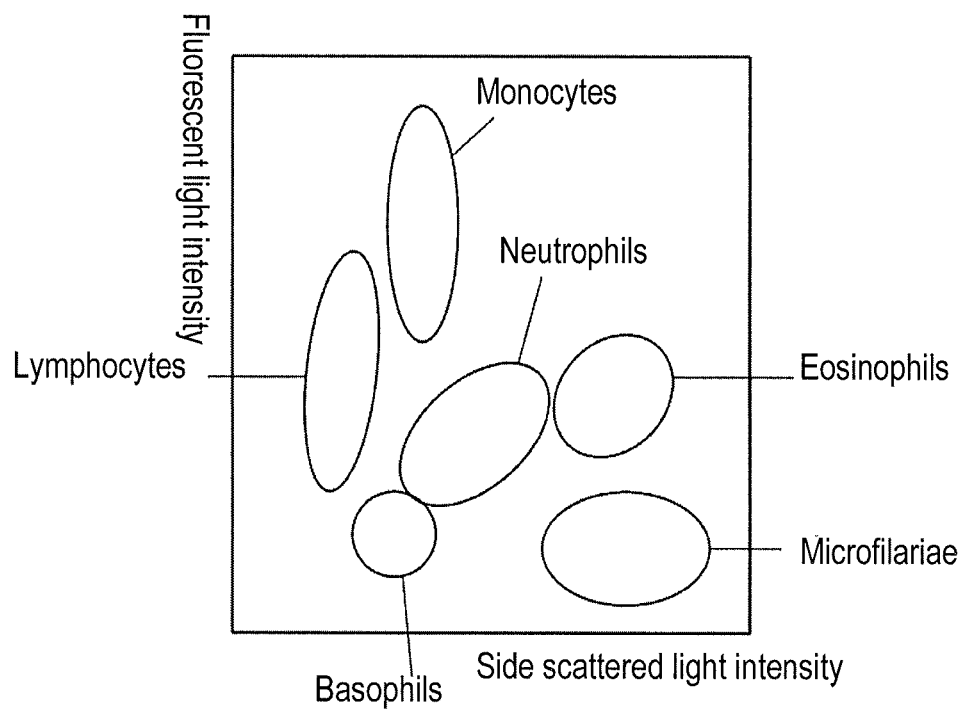
FIG. 6 is a scattergram of the side scattered light intensity and the fluorescent light intensity in the measurement data.

FIG. 6 schematically shows the regions of appearance of clusters in a scattergram plotted with the side scattered light intensity and fluorescent light intensity as the axes. An eosinophil cluster, neutrophil cluster, basophil cluster, lymphocyte cluster, monocyte cluster, and microfilaria cluster appear in the scattergram of FIG. 6. The CPU 51*a* discriminates white blood cells from microfilaria and classifies white blood cells as eosinophils, neutrophils, basophils, lymphocytes, and monocytes as shown in the scattergram of FIG. 6. Also in the process of step S9, the CPU 51*a* counts the number of white blood cells in each of the subclasses classified in this manner. The cluster of microfilaria does not influence the classification of white blood cells since there is no overlap with the clusters of the white blood cell subclasses.

In step S10, the CPU 51*a* determines whether the subject animal from whom the sample was collected is suspected of having filariasis based on the number of counted microfilaria (step S10). In this process, the determination is based on whether the counted number of microfilaria CN exceeds a predetermined standard value T. A suspicion of filariasis is determined when the number of microfilaria CVN exceeds the reference value T, and no suspicion of filariasis is determined when the number of microfilaria CN is less than the reference number.

In step S11, the CPU 51*a* stores the analysis result obtained above on the hard disk 51*d*. The CPU 51*a* then displays, on the display section 52, the analysis result screen indicating the analysis result stored on the hard disk 51*d* (step S12), and ends the process.

The numerical data such as number of particles (blood cells and microfilaria) and percentages obtained above are displayed together with a distribution diagram of the particles of the analysis result screen. The numerical data includes the count value of the lymphocytes, eosinophils, neutrophils, basophils, monocytes, and microfilaria, and the percentage of lymphocytes, eosinophils, neutrophils, basophils, monocytes relative to the total number of white blood cells. The distribution diagram includes a scattergram of the side scattered light intensity and fluorescent light intensity, a scattergram of the side scattered light intensity and forward scattered light intensity, and a scattergram of the forward scattered light pulse width and the forward scattered light intensity.

Figure 7:
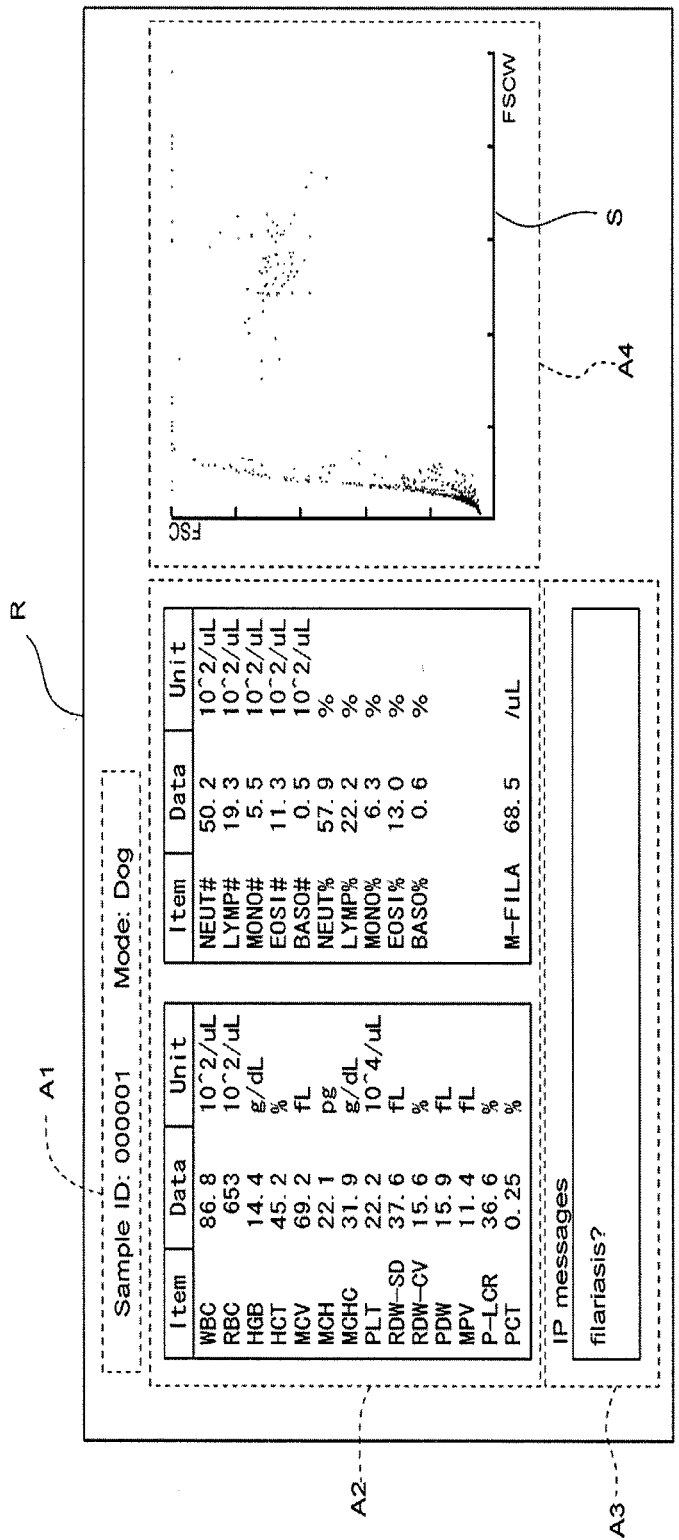
FIG. 7 shows an example of an analysis results screen.

FIG. 7 shows an example of an analysis result screen. As shown in FIG. 7, the analysis result screen R has display region A1 at the top part for showing the sample ID adhered to the sample and the species of animal (dog, cat and the like). Below the display region A1 is a display region A2 for showing the numerical data, a display region A3 for showing messages, and display region A4 for showing the distribution diagram.

The display region A2 shows numerical data such as the count values of white blood cells, red blood cells, platelets, neutrophils, lymphocytes, monocytes, eosinophils, basophils and the like (WBC, RBC, PLT, NEUT#, LYMP#, MONO#, EOSI#, BASO#), and the percentage of neutrophils, lymphocytes, monocytes, eosinophils, and basophils (NEUT#, LYMP#, MONO#, EOSI#, BASO#) relative to the total number of white blood cells. The count value of the microfilaria is shown in the item named M-FILA.

Display region A3 shows the message "filariasis?" when the determination is suspicion that the animal has filariasis in step S10 described above.

Display region A4 shows a scattergram used in filariae detection, that is, scattergram S using the forward scattered light pulse width and the forward scattered light intensity.

The operator can comprehend whether the animal is suspected of having filariasis via the message shown in display region A3 when the analysis result screen is displayed. The operator also can verify whether this determination is correct by confirming the scattergram S of display region A4 or the filaria count value shown in display region A2.

The operator also can determine whether the white blood cell count has been influenced by microfilaria by confirming the measurement results of the white blood cell subclasses. Alternatively, the operator can determine that the determination of the apparatus as to filariasis is correct by confirming the count value of the white blood cell subclasses. Since the eosinophils tend to increase in the case of filariasis infection, it also is possible to verify the analysis results based on the count and ratio of eosinophils.

The white blood cell classification mentioned above is one blood examination item almost always necessary in health diagnosis, and is a part of so-called screening to discriminate normal samples and sample with suspected abnormality. Since it is possible to test for the presence of filariasis at the same time as white blood cell classification in the present embodiment, screening for filariasis can be performed by the general health diagnostics without the separate conventional filaria test which uses direct microscopic examination or special test kit. Therefore, a sample suspected of being infected by filariasis can be screened during routine health diagnosis, and those filaria infected sample which are overlooked in conventional examination can be discovered and subjected to close examination. Filariasis also can be expected to be discovered in the early stages. Since the preparation of the measurement sample, detection of microfilaria, and determination of suspicion of filariasis is automated by the blood analyzer in the present embodiment, the burden on the operator is much reduced compared to conventional methods which employ direct microscopic examination or test kit. The blood analyzer of the present embodiment reduces costs since the measurement sample is prepared without using immunological techniques, and the rapidity of examination is improved by the use of flow cytometry.

The present method further surpasses conventional filaria examination methods in quantitative terms. Conventional filaria examinations using direct microscopy or special test kit are semi-quantitative or qualitative exams, the object of which is invariably to confirm the presence of infection, and until now there has not been an examination method to quantify the number of microfilaria in blood. Conventional treatments for filariasis determine the type of drug and dosage from the symptoms of the animal or semi-quantitative microfilariae index in peripheral blood; however, treatment policies concerning drug type and dosage can be suitably determined if it is possible to quantitatively asses the microfilariae. The filariae examination method of the present embodiment quantifies the number of filariae contained in a whole blood sample, and therefore can better contribute to determining proper treatment policy than conventional filariae examination methods.

Reagent consumption can be reduced since reagent is not consumed to simply detect microfilariae separately, since microfilariae detection and white blood cell classification are performed together in the measurement of one sample using the white blood cell classification reagent. In this way reagent preparation and wasteful processing are reduced to reduce the environmental burden. The environmental burden also is reduced by reducing the use of conventional test kits and stains used in direct microscopy. The present method also does not require test animals to obtain antibodies since the immunological methods of conventional immunological test kits are not employed.

Note that the above embodiment is described by way of example in which the forward scattered light pulse width and the forward scattered light intensity are combined as the combination of characteristic parameters suited for use in microfilariae detection, and by way of example of white blood cell classification using the combination of fluorescent light intensity and side scattered light intensity. Thus, a benefit of combining different characteristic parameters and white blood cell classification, particularly using the forward scattered light pulse width for microfilariae detection, is that microfilariae can be detected by focusing on the total length of the particles which differs most markedly between microfilariae and blood cells. Although abnormal blood cells (for example, immature lymphocytes and platelet aggregation) also may be in the blood due to complications of other diseases than microfilariae, microfilariae can be detected with a high degree of reliability even in samples that contain abnormal blood cells other than microfilariae because the total length of such abnormal blood cells is not comparable to that of microfilariae.

Therefore, although detecting microfilariae using the forward scattered light pulse width is most desirable, characteristic parameter other than the forward scattered light pulse width also may be used as shown in FIG. 6 because microfilariae can be discriminated from blood cells and detected without requiring the use of forward scattered light pulse width and without requiring mutually different characteristic parameters for microfilariae detection and white blood cell classification. Microfilariae also can be detected by a combination of fluorescent light intensity and side scattered light intensity as shown in S11 of FIG. 8 (described later), and microfilariae may be detected by a combination of forward scattered light intensity and side scattered light intensity as shown in S12 of FIG. 8 (described later).

Although microfilariae detection and white blood cell classification are performed using a measurement sample prepared for white blood cell classification in the above embodiment, it is to be noted that microfilariae detection need not be performed simultaneously with the white blood cell classification. A measurement sample also may be prepared for just microfilariae detection, and microfilariae may be detected from characteristic parameters obtained my measuring a measurement sample for measuring a total white blood cell count (WBC) without classifying the white blood cells as shown in S14 and S15 of FIG. 9 (described later).

<Verification Test>

The inventors performed tests to verify the performance of the method of detecting microfilariae in blood of the present embodiment (hereinafter referred to as "the present method"). The verification test is described below.

Samples collected from a filaria-infected animals (sample 1) and a normal samples (sample 2) were analyzed using a modified (modified software enabling measurements of microfilaria) multi-function automated blood cell analyzer XN-1000 made by Sysmex Corporation. Six samples were measured using the XN-1000 on both the WDF channel (white blood cell classification channel) and WNR channel (white blood cell and reticulocyte measurement channel). Reagents (hemolytic agent and staining reagent for the white blood cell classification specific to the XN-1000 were used in the measurements on the WDF channel, and reagents (hemolytic agent and staining reagent) for white blood cell and reticulocyte measurements specific to XN-1000 were used in measurements on the WNR channel.

Figure 8:
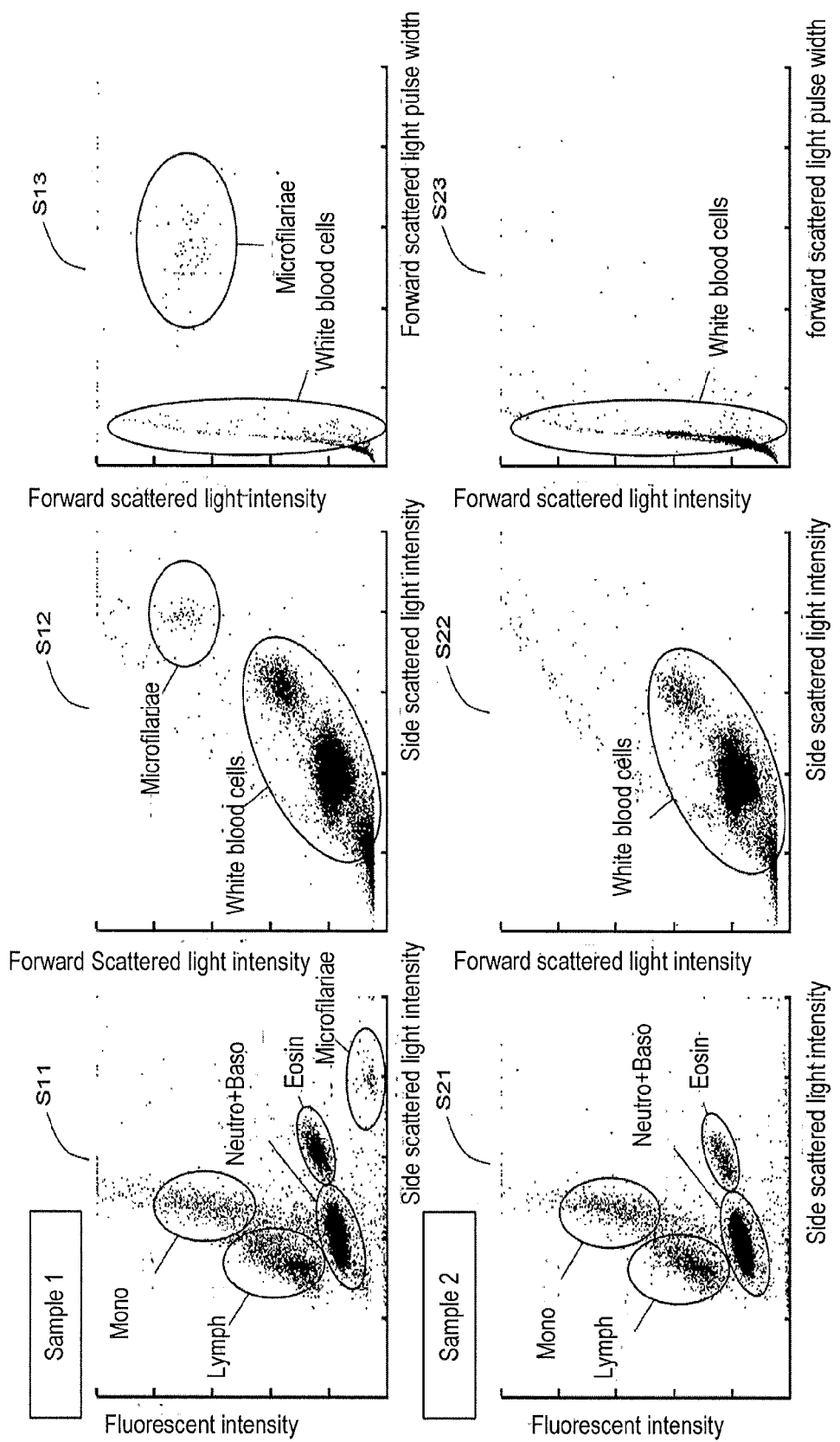
FIG. 8 shows scattergrams of the analyzed results in the XN-1000 WDF channel of a normal sample and a sample collected from an animal infected by filariasis.

FIG. 8 shows scattergrams of the analyzed results of samples 1 and 2 on the WDF channel. In FIG. 8, S11 is a scattergram of the side scattered light intensity and fluorescent light intensity of sample 1, S12 is a scattergram of the side scattered light intensity and forward scattered light intensity of sample 1, and S13 is a scattergram of the forward scattered light pulse width and forward scattered light intensity of sample 1. Furthermore, S21 is a scattergram of the side scattered light intensity and fluorescent light intensity of sample 2, S22 is a scattergram of the side scattered light intensity and forward scattered light intensity of sample 2, and S23 is a scattergram of the forward scattered light pulse width and forward scattered light intensity of sample 2.

As shown in FIG. 8, a cluster of lymphocytes, a cluster of monocytes, a cluster of eosinophils, a cluster of a blood cell groups constituted by neutrophils and basophils, and a microfilariae cluster appear at discrete positions in the scattergram S11. On the other hand, although a cluster of lymphocytes, a cluster of monocytes, a cluster of eosinophils, and a cluster of a blood cell groups constituted by neutrophils and basophils appear in the scattergram S21, no microfilariae cluster appears. Therefore, lymphocytes, monocytes, eosinophils, neutrophils, and basophils can be discriminated and microfilariae are detectable when side scattered light intensity and fluorescent light intensity are used on the WDF channel.

In the scattergram S12, a cluster of white blood cells (lymphocytes, monocytes, eosinophils, neutrophils, and basophils) and a cluster of microfilariae appear at discrete positions. On the other hand, although a cluster of white blood cells appears in the scattergram S22, a cluster of microfilariae does not appear. Therefore, it is understood that white blood cells can be discriminated and microfilariae can be detected also by using side scattered light intensity and forward scattered light intensity on the WDF channel.

In the scattergram S13, a white blood cell cluster and microfilariae cluster also appear at discrete positions. On the other hand, although a cluster of white blood cells appears in the scattergram S23, a cluster of microfilariae does not appear. Therefore, it is understood that white blood cells can be discriminated and microfilariae can be detected also by using side scattered light pulse width and forward scattered light intensity on the WDF channel.

In the scattergram S13, the white blood cells are entirely distributed on the forward scattered light intensity region (vertical axis), and the appearance region of the white blood cells and the appearance region of the microfilariae are concentrated on this axis. On the other hand, white blood cells appear in the low level region of the forward scattered light pulse width (horizontal axis), and microfilariae appear at a higher level in this region in comparison to the white blood cells with no concentration of either in this region. From this observation it is understood that white blood cells can be discriminated and microfilariae can be detected using only the forward scattered light pulse width on the WDF channel.

Figure 9:
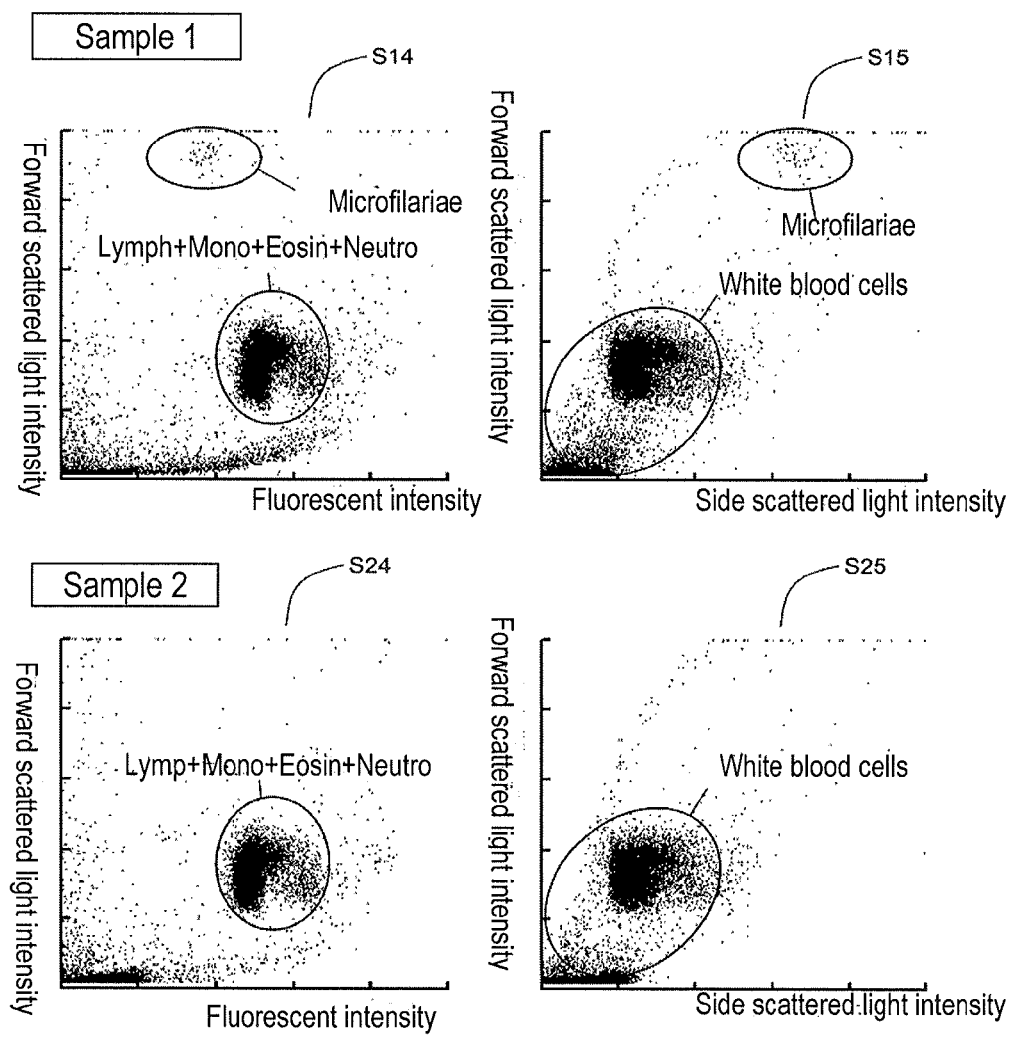
FIG. 9 shows scattergrams of the analyzed results in the XN-1000 WNR channel of a normal sample and a sample collected from an animal infected by filariasis.

FIG. 9 shows scattergrams of the analyzed results of samples 1 and 2 on the WNR channel. In FIG. 9, S14 is a scattergram of the fluorescent light intensity and forward scattered light intensity of sample 1, and S15 is a scattergram of the side scattered light intensity and forward scattered light intensity of sample 1. S24 is a scattergram of the fluorescent light intensity and forward scattered light intensity of sample 2, and S15 is a scattergram of the side scattered light intensity and forward scattered light intensity of sample 2.

As shown in FIG. 9, a cluster of blood cell groups constituted by lymphocytes, monocytes, eosinophils, and neutrophils, and a cluster of microfilariae appear at discrete positions in the scattergram S14. On the other hand, although a cluster of blood cell groups constituted by lymphocytes, monocytes, eosinophils, and neutrophils appear in the scattergram S24, no microfilariae cluster appears. Therefore, lymphocytes, monocytes, eosinophils, and neutrophils can be discriminated and microfilariae are detectable when side scattered light intensity and fluorescent light intensity are used on the WNR channel.

In the scattergram S15, a white blood cell cluster and microfilariae cluster also appear at discrete positions. On the other hand, although a cluster of white blood cells appears in the scattergram S25, a cluster of microfilariae does not appear. Therefore, it is understood that white blood cells can be discriminated and microfilariae can be detected also by using side scattered light intensity and forward scattered light intensity on the WNR channel.

Note that the inventors verified that white blood cells can be discriminated and microfilariae are detectable when using only forward scattered light pulse width on the WNR channel.

Then, the accuracy of the white blood cell count value when microfilariae and white blood cells were simultaneously detected using the same measurement sample was verified. The measurements performed using the XN-1000 on the WDF channel included calculating the number of eosinophils (EO#), neutrophils (NEUT#), basophils (BASO#), lymphocytes (LYMPH#), and monocytes (MONO#) together with the calculation of the number of microfilariae, and the respective percentage of eosinophils, neutrophils, basophils, lymphocytes, and monocytes (EO %, NEUT %, BASO %, LYMPH %, MONO %) relative to the total white blood cell count (WBC) were also calculated. The measurements performed by the XN-1000 on the WNR channel included calculating the number of microfilariae together with the white blood cell count (WBC). As comparative experiments of the present method, samples 1 and 2 were measured using a blood cell analyzer XT-4000i made by Sysmex Corporation and a blood cell analyzer Procyte DX made by IDEXX Laboratories, Inc. to obtain EO#, NEUT#, BASO#, LYMPH#, MONO#, EO %, NEUT %, BASO %, LYMPG %, MONO %, and WBC. The reagents specific to each of the respective apparatuses were used in the comparative experiments. The comparative results are shown in the table below.

also may be detected and infective larvae penetrating internally from a carrier also may be detected insofar as filarial larvae appear in blood.

Although the above embodiment is described in terms of a configuration to both detect microfilariae and classify white blood cells from one measurement sample, the present invention is not limited to this configuration. Configurations are also possible in which a measurement sample is prepared for white blood cell classification and another separate measurement sample is prepared for use in the detection of microfilariae, with the respective measurement samples being measured separately.

Although the above embodiment is described in terms of a configuration in which hemolytic agent is used in the measurement sample for detecting microfilariae, the present invention is not limited to this configuration. Microfilariae also may be detected without using hemolytic agent. In this case, although red blood cells appear in the region of low level fluorescent light intensity, microfilariae are detectable because the region in which the red blood cells appear differs

TABLE 1

|  | Model | WBC | NEUT# | LYMPH# | MONO# | EO# | BASO# | NEUT % | LYMPH % | MONO % | EO % | BASO % |
|---|---|---|---|---|---|---|---|---|---|---|---|---|
| Sample 1 | XN | 97.8 | 58.0 | 19.9 | 6.9 | 12.9 | 0.0 | 59.3 | 20.4 | 7.1 | 13.2 | 0.0 |
|  | XT | 101.8 | 57.3 | 27.0 | 4.1 | 13.2 | 0.1 | 56.3 | 26.6 | 4.1 | 13.0 | 0.1 |
|  | PDx | 93.0 | 54.0 | 20.5 | 5.8 | 12.1 | 0.6 | 58.2 | 22.0 | 6.2 | 13.0 | 0.6 |
| Sample 2 | XN | 85.5 | 58.6 | 16.0 | 5.9 | 5.0 | 0.0 | 68.5 | 18.8 | 6.9 | 5.8 | 0.0 |
|  | XT | 86.5 | 56.5 | 22.4 | 2.5 | 4.9 | 0.2 | 65.3 | 25.9 | 2.9 | 5.6 | 0.2 |
|  | PDx | 84.9 | 59.0 | 15.9 | 5.1 | 4.6 | 0.3 | 69.5 | 18.7 | 6.0 | 5.4 | 0.4 |

In the case of sample 1, the calculated value of the white blood cell count by the XN-1000 was substantially the same as the calculated values by the XT-4000i and Procyte DX. That is, it is to be understood that the present method accurately measured microfilariae at the same time the total white blood cell count and classification of white blood cell subclasses were performed.

Figure 10:
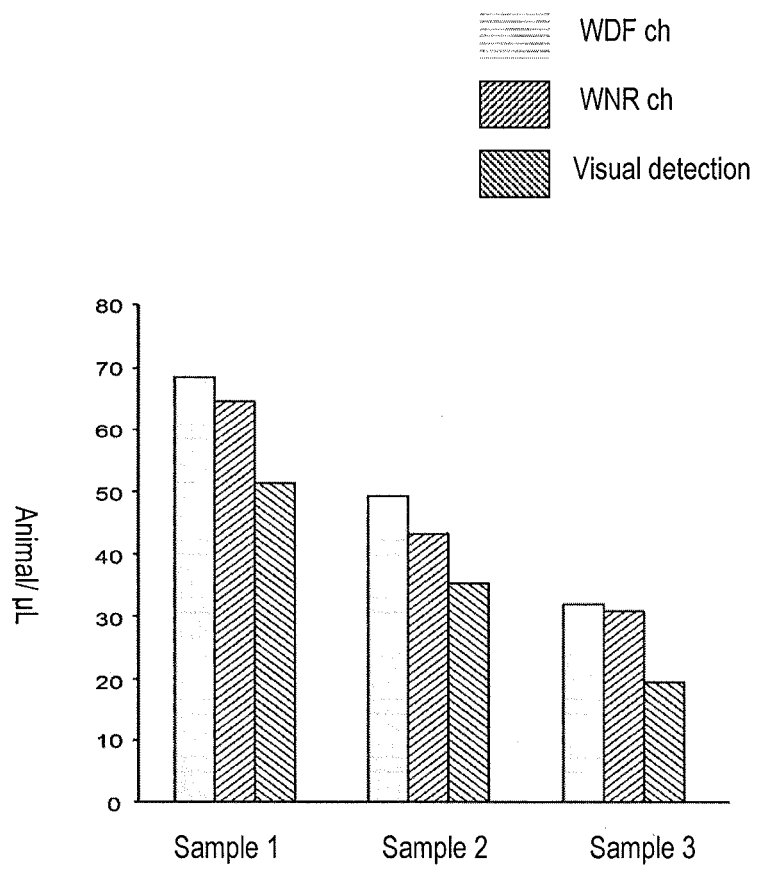
FIG. 10 is a graph comparing the XN-1000 WDF channel, WNR channel, and visual microfilaria measurement values of three samples collected from filariasis infected animals.

Thereafter, three filariae-infected samples (the sample 1 mentioned above, and samples 3 and 4) were analyzed using the XN-1000 and the analysis results were compared. FIG. 10 is a graph comparing the measured values of microfilariae in samples 1, 3, and 4 obtained by using the WDF channel and WNR channel of the XN-1000 and visual observation.

As shown in FIG. 10, in the visual detection method (hereinafter referred to as "microscopy method") the number of microfilariae in the 1 μL sample was 51.6 in sample 1, 35.2 in sample 3, and 19.4 in sample 4, the number gradually decreasing in the order sample 1, 3, 4. In contrast, the detection results of the present method on the WDF channel were 68.5 for sample 1, 49.4 for sample 3, and 31.9 for sample 4. The detection results of the present method on the WNR channel were 64.7 for sample 1, 43.3 for sample 3, and 30.9 for sample 4. That is, although the respective numerical values are larger than those obtained by the microscopy method, in the present method, the results obtained on the WDF channel and WNR channel using the present method are decreasing in the order of sample 1, 3, 4, which are noted to correlate with the results by the microscopy method. The present method therefore is understood to have sufficient quantitative precision.

(Other Embodiments)

Note that although the above embodiment is described by way of example of detecting microfilariae as filarial larvae present in blood, sheathed larvae (broadly, microfilariae)

from the region in which microfilariae appear. Microfilariae also are detectable when the sample also can be measured without using a staining reagent. In this case, the microfilariae can be detected by using the forward scattered light pulse width, and by using the side scattered light intensity and forward scattered light intensity.

Figure 11:
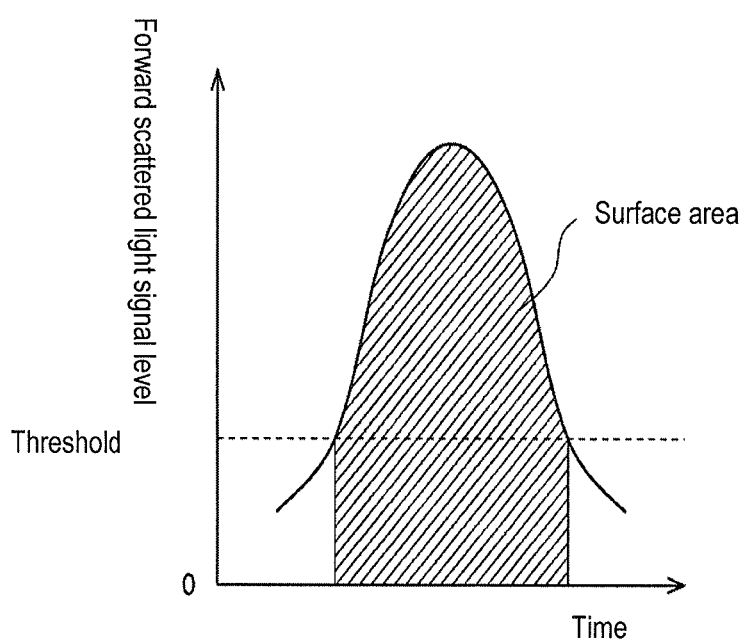
FIG. 11 is a graph of the pulse signals which schematically illustrate other characteristic parameters of the forward scattered light.

The above embodiment is described in terms of a configuration in which microfilariae are detected using combinations of forward scattered light pulse width, forward scattered light intensity, side scattered light intensity, and fluorescent light intensity, however, the present invention is not limited to this configuration. Rather than forward scattered light pulse width, the side scattered light pulse width or fluorescent light pulse width also may be used. Other characteristic parameters reflecting the total length of the particle also may be used instead of the scattered light and fluorescent light pulse width. FIG. 11 is a graph of the pulse signals which schematically illustrate an example of other characteristic parameters of the forward scattered light. As shown in FIG. 11, for example, the area under the curve of the pulse which exceeds a predetermined threshold value also may be used as the characteristic parameter to detect microfilariae.

The above embodiment is described in terms of a configuration providing a fixed gate G for microfilariae detection wherein particles present within the gate G are detected as microfilariae, however, the present invention is not limited to this configuration. A configuration is possible in which microfilariae are detected and discriminated from other particles by clustering particles via the method disclosed in U.S. Pat. No. 5,555,196. U.S. Pat No. 5,555,196 is incorporated in the present specification for reference.

Although the above embodiment is described in terms of a configuration providing a fixed gate G for microfilariae detection unrelated to species, gates G for microfilariae detected respectively corresponding to a plurality of species also may be used. In this case, the numerical ranges defining the gates respectively corresponding to the plurality of species may be pre-stored on the hard disk 51d, so that the gate corresponding to the species specified by the operator can be read therefrom and applied to the analysis of microfilariae detection. The reference value T used to discriminate filariasis morbidity used in step S10 of FIG. 4 also may be set as a value which differs by species [needs period]

Although the above embodiment is described in terms of a configuration in which the controller 25 controls the operation of each part of the measuring unit 2 and the CPU 51a performs an analysis process on measurement data, the present invention is not limited to this configuration. A configuration also is possible in which the control of the operation of each part of measuring unit 2 and execution of the analysis process of measurement data are accomplished by a single controller (CPU). In this case, a single apparatus may integrate the functions of the measuring unit 2 and the information processing unit 5 rather than providing the measuring unit 2 and the information processing device 5 separately.

Although a single computer 5a performs all processing of the computer program 54a in the above embodiment, the present invention is not limited to this configuration inasmuch as processes identical to those of the computer program 54a also may be distributed and executed by a plurality of devices (computers) as a distributed system.

The method, blood analyzer, and computer program for detecting filarial larvae in blood the present invention may be used as a method, blood analyzer, and computer program for detecting filarial larvae in the blood of an animal such as a dog.

What is claimed is:

1. A method of detecting filarial larvae in blood without using an immunological technique, comprising:
   without using an immunological technique, preparing a measurement sample from a blood sample collected from an animal;
   flowing the prepared measurement sample through a flow cell;
   irradiating light to the measurement sample flowing through the flow cell;
   detecting first scattered light, second scattered light different from the first scattered light and fluorescent light all scattered from the measurement sample;
   converting the first and second scattered light and the fluorescent light, respectively, into a first series of pulse signals, a second series of pulse signals and a third series of pulse signals, the pulse signals each being representative of an event indicative of passing of a particle contained in the measurement sample, wherein each event is valued with a width of a corresponding pulse and a height thereof;
   gating, for distinguishing filarial larvae from white blood cells in the measurement sample, events represented by at least one of the first, second and third series of pulse signals to identify a plurality of discrete populations of events to thereby detect a first group of events indicative of passing of filarial larvae contained in the measurement sample and a second group of events indicative of passing of white blood cells in the measurement sample
   counting the first group of events indicative of passing of filarial larvae contained in the measurement sample; and
   displaying a count of the first group of events,
   wherein gating events represented by at least one of the first, second and third series of pulse signals comprises (i) gating the events in a one-dimensional distribution of widths represented by one of the first, second and third series of pulse signals, (ii) gating the events in a two-dimensional distribution of two groups of heights represented, respectively, by two of the first, second and third series of pulse signals or (iii) gating the events in a two-dimensional distribution of widths and heights represented by the first series of pulse signals.

2. The method of claim 1, wherein gating events represented by at least one of the first, second and third series of pulse signals comprises identifying the first group of events with a first gate for defining a range of widths shifted in a wider width direction from a range of widths defined by a second gate used to identify the second group of events.

3. The method of claim 1, wherein gating events represented by at least one of the first, second and third series of pulse signals comprises gating a two-dimensional distribution of two groups of heights of the events represented, respectively, by the second and third series of pulse signals to identify subpopulations of the second group of events.

4. The method of claim 3, wherein
   counting the first group of events further comprises counting each of the subpopulations of the second group of events, and
   displaying a count of the first group of events comprises displaying counts of the subpopulations of the second group of events.

5. The method of claim 1, wherein the animal is one of a dog, a cat and a rabbit.

6. The method of 1, wherein the method is automatically performed using an automated blood cell analyzer.

7. The method of claim 1, further comprising counting the second group of events.

8. The method of claim 1, wherein gating events represented by at least one of the first, second and third series of pulse signals comprises gating a two-dimensional distribution of widths and heights of the events represented by the first series of pulse signals.

9. The method of claim 1, wherein gating events represented by at least one of the first, second and third series of pulse signals comprises gating a two-dimensional distribution of two groups of heights of the events represented, respectively, by the first and third series of pulse signals.

10. The method of claim 1, wherein gating events represented by at least one of the first, second and third series of pulse signals comprises gating a two-dimensional distribution of two groups of heights of the events represented, respectively, by the first and second series of pulse signals.

11. The method of claim 1, wherein counting the first group of events further comprise counting of the second group of events indicative of passing of white blood cells in the measurement sample, and displaying a count of the first group of events further comprises displaying a count of the second group of events.

12. The method of claim 1, wherein displaying a count of the first group of events further comprising displaying distributions of the first and second groups of events.

13. The method of claim 1, wherein preparing the measurement sample comprises preparing the measurement sample exclusive of antibody.

14. The method of claim 1, wherein the first and second scattered lights are forward and side scattered light, respectively.

* * * * *

UNITED STATES PATENT AND TRADEMARK OFFICE
CERTIFICATE OF CORRECTION

PATENT NO. : 9,541,542 B2  
APPLICATION NO. : 14/583453  
DATED : January 10, 2017  
INVENTOR(S) : Seiichiro Tsuchiya et al.

It is certified that error appears in the above-identified patent and that said Letters Patent is hereby corrected as shown below:

In the Claims

In Column 16, Claim 6, Line 32, after "The method" replace "of 1," with --of claim 1,--.

Signed and Sealed this  
Twentieth Day of June, 2017

Joseph Matal  
*Performing the Functions and Duties of the*  
*Under Secretary of Commerce for Intellectual Property and*  
*Director of the United States Patent and Trademark Office*